US012685779B2

(12) United States Patent
Harada et al.

(10) Patent No.: US 12,685,779 B2
(45) Date of Patent: Jul. 21, 2026

(54) COMPLEX

(71) Applicant: UNITED IMMUNITY, CO., LTD., Tokyo (JP)

(72) Inventors: Naozumi Harada, Tokyo (JP); Tadashi Inoue, Tokyo (JP); Takatoshi Soga, Tokyo (JP); Ayaka Matsumoto, Tokyo (JP)

(73) Assignee: UNITED IMMUNITY, CO., LTD., Tokyo (JP)

( * ) Notice: Subject to any disclaimer, the term of this patent is extended or adjusted under 35 U.S.C. 154(b) by 0 days.

(21) Appl. No.: 19/108,248

(22) PCT Filed: May 31, 2024

(86) PCT No.: PCT/JP2024/019982

§ 371 (c)(1),
(2) Date: Mar. 3, 2025

(87) PCT Pub. No.: WO2024/248117

PCT Pub. Date: Dec. 5, 2024

(65) Prior Publication Data

US 2025/0255974 A1 Aug. 14, 2025

(30) Foreign Application Priority Data

Jun. 1, 2023 (JP) ................................. 2023-090696
Sep. 21, 2023 (JP) ................................. 2023-155586

(51) Int. Cl.
*A61K 47/61* (2017.01)

(52) U.S. Cl.
CPC .................................... *A61K 47/61* (2017.08)

(58) Field of Classification Search
CPC ..... A61K 47/61; A61K 31/437; A61K 31/719
See application file for complete search history.

(56) References Cited

U.S. PATENT DOCUMENTS

| | | | | |
|---|---|---|---|---|
| 9,833,407 | B2 | 12/2017 | Yuki et al. | |
| 2008/0166369 | A1 | 7/2008 | Shiku et al. | |
| 2013/0230578 | A1* | 9/2013 | Wightman | A61P 31/16 424/277.1 |
| 2019/0111078 | A1 | 4/2019 | Shiku et al. | |
| 2023/0201263 | A1 | 6/2023 | Shiku et al. | |

FOREIGN PATENT DOCUMENTS

| | | | |
|---|---|---|---|
| JP | 2009-149526 | 7/2009 | |
| JP | 2013-534248 | 9/2013 | |
| JP | 2019-530658 | 10/2019 | |
| WO | 2006/077724 | 7/2006 | |
| WO | 2012/024284 | 2/2012 | |
| WO | 2021/231942 | 11/2012 | |
| WO | WO-2013085021 A1 * | 6/2013 | A61K 39/39 |
| WO | 2014/054588 | 4/2014 | |
| WO | 2017/138557 | 8/2017 | |
| WO | 2018/045058 | 3/2018 | |

OTHER PUBLICATIONS

International Search Report issued Aug. 13, 2024 in International (PCT) Application No. PCT/JP2024/019982.
Decision to Grant a Patent issued Oct. 8, 2024, in corresponding Japanese Application No. 2024-553181, with English translation.
Huang et al., "Recent trends in the development of Toll-like receptor 7/8-targeting therapeutics", Expert Opinion on Drug Discovery, 2021, vol. 16, No. 8, pp. 869-880.
Singh et al., "Pullulan and pullulan derivatives as promising biomolecules for drug and gene targeting", Carbohydrate Polymers, 2015, vol. 123, pp. 190-207.
Mullins et al., "Intratumoral immunotherapy with TLR7/8 agonist MEDI9197 modulates the tumor microenvironment leading to enhanced activity when combined with other immunotherapies", Journal for Immuno Therapy of Cancer, 2019, vol. 7, No. 1.
Extended European Search Report dated Sep. 17, 2025 in corresponding European Patent Application No. 24815597.0.

* cited by examiner

*Primary Examiner* — James W Rogers
(74) *Attorney, Agent, or Firm* — Wenderoth, Lind & Ponack, L.L.P.

(57) ABSTRACT

An object is to provide a technique that improves the poor solubility of a compound of formula (1) in water and further suppresses the cytokine excessive release action and bone marrow toxicity of the compound of formula (1). This object is achieved by a complex comprising a modified polysaccharide containing a hydrophobic group, and a compound represented by formula (1).

7 Claims, 7 Drawing Sheets

COMPLEX

TECHNICAL FIELD

The present invention relates to a complex.

BACKGROUND ART

The importance of immune cells, particularly macrophages (tumor-associated macrophages, abbreviated as "TAMs"), in cancer tissues has been pointed out as a factor influencing the malignancy of cancer. When TAMs are M2-dominant, they act immunosuppressively and create a microenvironment favorable for cancer growth. If their dominance can be changed to M1-dominance, cancer growth inhibitory effects can be expected.

It has been reported that Toll-like receptor 7 and Toll-like receptor 8 (respectively abbreviated as TLR7 and TLR8) activators polarize macrophages from M2-like to M1-like. In addition, various compounds are known as TLR7 and TLR8 activators currently under development (NPL 1).

CITATION LIST

Non-Patent Literature

NPL 1: Expert Opin Drug Discov. 2021 August; 16(8): 869-880.

SUMMARY OF INVENTION

Technical Problem

General TLR7/8 agonists cannot be administered systemically due to issues with excessive cytokine release and bone marrow toxicity that occur when administered systemically. In particular, compounds of formula (1) described below, such as Telratolimod, have relatively long hydrocarbon chains and are thus poorly soluble in water. In the course of research, the present inventor also newly found, through formulation studies, that Telratolimod has cytokine excessive release action and bone marrow toxicity.

An object of the present invention is to provide a technique that suppresses the excessive cytokine release action and bone marrow toxicity of various TLR7/8 activators and enables their systemic administration.

Solution to Problem

As a result of intensive research on various TLR7/8 agonists in view of the above object, the present inventor found that a complex comprising a modified polysaccharide containing a hydrophobic group, and a compound represented by formula (1) can achieve the above object. As a result of still further research based on this finding, the present inventor has completed the present invention. Specifically, the present invention includes the following aspects.

Item 1. A complex comprising a modified polysaccharide containing a hydrophobic group, and a compound represented by formula (1):

(1)

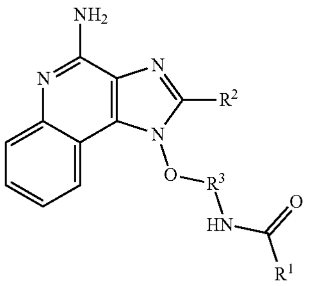

wherein $R^1$ is a $C_{12-25}$ linear alkyl group, $R^2$ is a $C_{2-8}$ linear alkyl group, and $R^3$ is a $C_{2-8}$ linear alkylene group.

Item 2. The complex according to Item 1, wherein the polysaccharide that forms the modified polysaccharide comprises pullulan.

Item 3. The complex according to Item 1 or 2, wherein the hydrophobic group comprises a hydrophobic group having a sterol skeleton.

Item 4. The complex according to any one of Items 1 to 3, wherein the modified polysaccharide has a weight average molecular weight of 5000 to 2,000,000.

Item 5. The complex according to any one of Items 1 to 4, wherein $R^1$ is a $C_{15-19}$ linear alkyl group, $R^2$ is a $C_{3-5}$ linear alkyl group, and $R^3$ is a $C_{3-5}$ linear alkylene group.

Item 6. The complex according to Item 5, wherein the compound is Telratolimod.

Item 7. The complex according to any one of Items 1 to 6, which is gel particles.

Item 8. The complex according to Item 7, wherein the compound is contained within the gel particles.

Item 9. The complex according to any one of Items 1 to 8, wherein the mass ratio of the modified polysaccharide to the compound (mass of modified polysaccharide/mass of compound) is 2 to 20.

Item 10. The complex according to any one of Items 1 to 9, which has a scattering intensity average particle size of 10 to 200 nm.

Item 11. A drug comprising the complex according to any one of Items 1 to 10.

Item 12. The drug according to Item 11, which is a cancer therapeutic agent.

Item 12A. A cancer treatment method comprising administering the complex according to any one of Items 1 to 10 to a subject (e.g., a subject with cancer).

Item 12B. The complex according to any one of Items 1 to 10 for use in cancer treatment.

Item 12C. Use of the complex according to any one of Items 1 to 10 for producing a cancer therapeutic agent.

Item 12D. Use of the complex according to any one of Items 1 to 10 as a cancer therapeutic agent.

Item 13. The drug according to Item 11 or 12, which is a macrophage polarizing agent.

Item 13A. A macrophage polarization method comprising administering the complex according to any one of Items 1 to 10 to a subject (e.g., a subject with cancer).

Item 13B. The complex according to any one of Items 1 to 10 for use in macrophage polarization.

Item 13C. Use of the complex according to any one of Items 1 to 10 for producing a macrophage polarizing agent.

Item 13D. Use of the complex according to any one of Items 1 to 10 as a macrophage polarizing agent.

Item 14. The complex according to any one of Items 1 to 10, or the drug according to any one of Items 11 to 13, which is used in combination with an immune checkpoint inhibitor.

Advantageous Effects of Invention

The present invention can provide a pharmaceutical composition relating to antitumor agents etc., which suppresses the excessive cytokine release action and bone marrow toxicity of TLR7/8 agonists and enables their systemic administration.

DESCRIPTION OF EMBODIMENTS

Figure 1:
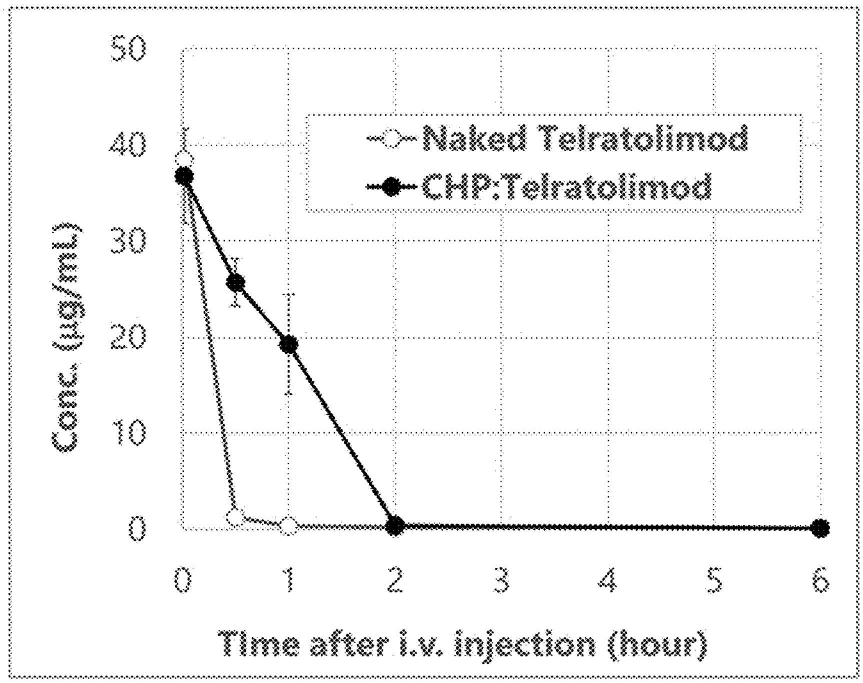
FIG. 1 shows the results of Test Example 4. The vertical axis indicates the Telratolimod concentration in serum, and the horizontal axis indicates the time elapsed since the administration of test drugs. The legend indicates test drugs; "Naked Telratolimod" refers to a test drug that is not encapsulated in cholesterol-modified pullulan nanogel (hereinafter, "CHP nanogel"), and "CHP:Telratolimod" refers to a test drug coated with CHP nanogel.

In the present specification, the terms "comprise" and "contain" include the concepts of "comprise," "contain," "essentially consist of," and "consist of."

1. Complex

In an embodiment, the present invention relates to a complex comprising a modified polysaccharide containing a hydrophobic group, and a compound represented by formula (1):

(1)

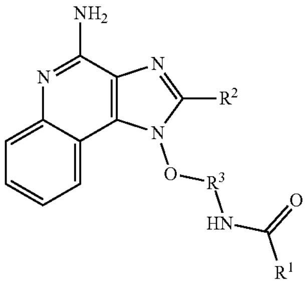

(in the present specification, also referred to as "the complex of the present invention"). This is described below.

The compound represented by formula (1) is as described below.

In formula (1), $R^1$ is a $C_{12-25}$ linear alkyl group. The number of carbon atoms in the linear alkyl group is preferably 14 to 23, more preferably 14 to 21, even more preferably 15 to 19, still even more preferably 16 to 18, and particularly preferably 17.

In formula (1), $R^2$ is a $C_{2-8}$ linear alkyl group. The number of carbon atoms in the linear alkyl group is preferably 2 to 6, more preferably 3 to 5, and particularly preferably 4.

In formula (1), $R^3$ is a $C_{2-8}$ linear alkylene group. The number of carbon atoms in the linear alkylene group is preferably 2 to 6, more preferably 3 to 5, and particularly preferably 4.

The compound represented by formula (1) is particularly preferably Telratolimod (a compound wherein $R^1$ is a $C_{17}$ linear alkyl group, $R^2$ is a $C_4$ linear alkyl group, and $R^3$ is a $C_4$ linear alkylene group).

The compound represented by formula (1) can be in the form of a salt. The salt is not particularly limited as long as it is a pharmaceutically acceptable salt, and may be, for example, an acid addition salt. Specific examples of such salts include acid addition salts with mineral acids, such as hydrochloric acid, hydrobromic acid, hydroiodic acid, sulfuric acid, nitric acid, and phosphoric acid; with organic acids, such as formic acid, acetic acid, propionic acid, oxalic acid, malonic acid, malic acid, tartaric acid, fumaric acid, succinic acid, lactic acid, maleic acid, citric acid, methanesulfonic acid, trifluoromethanesulfonic acid, and ethanesulfonic acid; and with acidic amino acids, such as aspartic acid and glutamic acid.

The compound represented by formula (1) can be in the form of a solvate. The solvate is not particularly limited as long as it is a pharmaceutically acceptable salt, and examples include solvates with solvents such as water, ethanol, glycerol, and acetic acid.

The compound represented by formula (1) used can be a commercially available product or a product obtained according to a known production method.

The compounds represented by formula (1) can be used singly or in combination of two or more.

The modified polysaccharide is a compound obtained by modifying a polysaccharide, and is not particularly limited as long as it contains a hydrophobic group as a modifying group. In the present invention, it was found that the formation of a complex with a modified polysaccharide can improve the poor solubility of the compound of formula (1) in water, and can further suppress the excessive cytokine release action and bone marrow toxicity of the compound of formula (1).

The polysaccharide that forms the modified polysaccharide (i.e., polysaccharide before modification) is not particularly limited as long as it is a polymer to which a sugar residue is glycosidically linked. Usable examples of sugar residues that form the polysaccharide include residues derived from sugars, such as monosaccharides (e.g., glucose, mannose, galactose, and fucose), disaccharides, or oligosaccharides. The sugar residue may be 1,2-, 1,3-, 1,4-, or 1,6-glycosidically linked, and the linkage thereof may be either an α- or β-linkage. Further, the polysaccharide may be liner or branched. Preferable sugar residues are glucose residues. Preferable polysaccharides are, for example, naturally occurring or synthetic pullulan, mannan, dextran, amylose, amylopectin, and the like. Among these, from the viewpoint of the effect of improving poor solubility, the effect of suppressing excessive cytokine release action and bone marrow toxicity, anticancer effects, macrophage polarization effects, etc., preferred are pullulan, mannan, dextran, etc., more preferred are pullulan, mannan, etc., and particularly preferred are pullulan etc.

The weight average molecular weight of the polysaccharide is not particularly limited as long as the modified polysaccharide can form gel particles, but is 5,000 to 2,000,000, for example. The weight average molecular weight of the polysaccharide is preferably 10,000 to 1,000,000, more preferably 20,000 to 500,000, even more preferably 40,000 to 250,000, and still even more preferably 80,000 to 125,000.

The polysaccharide used can be a commercially available product or a product obtained according to a known production method.

The hydrophobic group is not particularly limited as long as it is a group with hydrophobicity. From the viewpoint of the effect of improving poor solubility, the effect of suppressing excessive cytokine release action and bone marrow toxicity, anticancer effects, macrophage polarization effects, etc., the hydrophobic group is preferably a hydrophobic group having a sterol skeleton, a hydrocarbon group, or the like, and particularly preferably a hydrophobic group having a sterol skeleton.

The sterol skeleton is an alcohol in which a hydroxy group is attached to a cyclopentahydrophenanthrene ring shown in formula (I). Symbols A to D in formula (I) represent each ring that forms the cyclopentahydrophenanthrene ring.

(I)

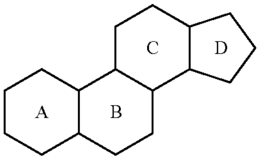

In the sterol skeleton, the cyclopentahydrophenanthrene ring may have a double bond, and the bonding position of the hydroxyl group is not limited. Preferable are either sterols with a hydroxy group at the C-3 position and a double bond in the B ring, or stanols with a hydroxy group at the C-3 position and a saturated ring. Examples of the hydrophobic group having a sterol skeleton include groups derived from compounds with a modified sterol skeleton, for example, the ring-forming carbon is replaced by a hydrocarbon group (e.g., a $C_{1-20}$ linear or branched alkyl group). The phrase "group derived from" refers to a group of a compound from which a hydrogen atom or a functional group, such as a hydroxyl group, is removed.

Examples of the hydrophobic group having a sterol skeleton include cholesterol-derived groups, cholestanol-derived groups, lanosterol-derived groups, ergosterol-derived groups, β-sitosterol-derived groups, campesterol-derived groups, stigmasterol-derived groups, brassicasterol-derived groups, and the like. Preferred among these are sterol-derived groups, such as cholesterol-derived groups, cholestanol-derived groups, lanosterol-derived groups, and ergosterol-derived groups; and more preferred are cholesterol-derived groups.

Examples of the hydrocarbon group as a hydrophobic group include, but are not particularly limited to, $C_{8-50}$ (preferably $C_{10-30}$, more preferably $C_{1-20}$) chain (preferably linear) hydrocarbon groups (preferably alkyl groups).

The weight average molecular weight of the modified polysaccharide is not particularly limited as long as the modified polysaccharide can form gel particles, but is 5,000 to 2,000,000, for example. The weight average molecular weight of the modified polysaccharide is preferably 10,000 to 1,000,000, more preferably 20,000 to 500,000, even more preferably 40,000 to 250,000, and still even more preferably 80,000 to 125,000.

The number of hydrophobic groups contained in the modified polysaccharide is not particularly limited as long as the modified polysaccharide can form gel particles, and is, for example, 1 to 10, and preferably 1 to 5, per 100 sugar residues that form the polysaccharide.

The hydrophobic group can be linked to the polysaccharide directly or indirectly (e.g., through a linker).

The modified polysaccharide is preferably, for example, one containing 1 to 10 (preferably 1 to 5) sugar units per 100 sugar residues that form the polysaccharide, whose primary hydroxyl group is represented by formula (II): $—O—(CH_2)_x CONH(CH_2)_yNH—CO—O—R$ (II), wherein R is a hydrophobic group having a sterol skeleton or a hydrocarbon group, x is 0 or 1, and y is any positive integer. y is preferably 1 to 8.

The modified polysaccharide can be synthesized by or according to a known method (e.g., WO00/12564). For example, the following method can be used. First, CU-so hydroxyl group-containing hydrocarbon or sterol, and a diisocyanate compound represented by formula $OCN—R^ANCO$, wherein $R^A$ is $C_{1-50}$ hydrocarbon group, are reacted to produce an isocyanato group-containing hydrophobic compound in which one molecule of $C_{12-50}$ hydroxyl group-containing hydrocarbon or sterol is reacted. Then, the resulting isocyanato group-containing hydrophobic compound and a polysaccharide are further reacted to produce a hydrophobic group-containing polysaccharide containing a $C_{12-50}$ hydrocarbon group or a stearyl group as a hydrophobic group. The obtained reaction product is purified with a ketone solvent, whereby a high-purity hydrophobic group-containing polysaccharide can be produced.

The modified polysaccharides can be used singly or in combination of two or more.

The mass ratio of the modified polysaccharide to the compound of formula (1) (mass of modified polysaccharide/mass of compound of formula (1)) is preferably 1 or more, more preferably 2 to 20, even more preferably 3 to 10, and still even more preferably 3 to 8. The mass ratio within the above range makes it possible to exhibit even greater anticancer effects and macrophage polarization effects.

The complex of the present invention may be gel particles. The term "gel particles" refers to polymer gel particles with a hydrogel structure. The term "hydrogel" refers to a three-dimensional network structure formed by cross-linking of hydrophilic polymers and swelling with water. In the complex of the present invention as gel particles, the modified polysaccharide is self-assembled through physical crosslinks formed based on hydrophobic interactions with the hydrophobic group, forming a three-dimensional network structure. When the complex of the present invention is gel particles, the compound of formula (1) is preferably contained within the gel particles.

The shape of the complex of the present invention is not particularly limited, but is generally spherical.

The complex of the present invention is preferably nano-sized (preferably nanogel particles), and the scattering intensity average particle size thereof is, for example, 200 nm or less, preferably 10 to 200 nm, more preferably 20 to 200 nm, even more preferably 60 to 190 nm, still even more preferably 80 to 180 nm, and particularly preferably 90 to 160 nm. The particle size can be measured by a dynamic light scattering method.

The complex of the present invention may contain substances other than the modified polysaccharide. Examples of other substances include proteins, peptides, nucleic acids, sugars, low-molecular-weight compounds, high-molecular-weight compounds, and minerals, as well as complexes thereof. More specifically, examples of other substances include adjuvants, cancer antigens, anticancer agents, nucleic acid drugs, and other drugs.

Adjuvants can be selected from inactivated bacteria, bacterial extracts, nucleic acid lipopolysaccharides, lipopeptides, synthetic low-molecular-weight compounds, and the like. Preferably, imidazoquinolines (e.g., R848 and imiquimod), saponins (e.g., QuilA and QS21), STING agonists (e.g., cyclic di-GMP), monophosphoryl lipids, lipopeptides, and the like are used. In addition to the above, examples of adjuvants include taxane drugs, anthracycline drugs, JAK/STAT inhibitors, indole deoxygenase (IDO) inhibitors, tryptophan deoxygenase (TDO) inhibitors, and the like. These inhibitors include compounds that have antagonistic activity against these factors, as well as neutralizing antibodies against these factors.

Cancer antigens include antigenic polypeptides, and are preferably antigenic polypeptides. Antigen polypeptides are antigens or partial peptides thereof that are highly expressed in cancer cells, and that are, in some cases, only expressed by cancer cells. Antigenic polypeptides can be expressed within or on the surface of cancer cells.

Antigenic polypeptides can be selected from, but are not limited to, ERK1, ERK2, MART-1/Melan-A, gp100, adenosine deaminase binding protein (ADAbp), FAP, cyclophilin B, colorectal-associated antigen (CRC)-C017-1A/GA733, carcinoembryonic antigen (CEA), CAP-1, CAP-2, etv6, AML1, prostate-specific antigen (PSA), PSA-1, PSA-2, PSA-3, prostate-specific membrane antigen (PSMA), T-cell receptor/CD3-zeta chain, CD20, MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4(MAGE-B4), MAGE-C1, MAGE-C2, MAGE-C3, MAGE-C4, MAGE-C5, GAGE-1, GAGE-2, GAGE-3, GAGE-4, GAGE-5, GAGE-6, GAGE-7, GAGE-8, and GAGE-9, BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100Pmel117, PRAME, NY-ESO-1, cdc27, adenomatous polyposis coli protein (APC), fodrin, connexin 37, Ig idiotype, p15, gp75, GM2 ganglioside, GD2 ganglioside, human papillomavirus protein, Smad family of tumor antigens, lmp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1, CT-7, CD20, c-erbB-2, and partial peptides thereof.

Examples of anticancer agents include alkylating agents, metabolic antagonists, microtubule inhibitors, antibiotic anticancer agents, topoisomerase inhibitors, platinum agents, molecular target drugs, hormonal agents, biologics, and the like.

Examples of alkylating agents include cyclophosphamide, ifosfamide, nitrosoureas, dacarbazine, temozolomide, nimustine, busulfan, melphalan, procarbazine, ranimustine, and the like.

Examples of metabolic antagonists include enocitabine, carmofur, capecitabine, tegafur, tegafur-uracil, tegafur-gimeracil-oteracil potassium, gemcitabine, cytarabine, cytarabine ocfosfate, nelarabine, fluorouracil, fludarabine, pemetrexed, pentostatin, methotrexate, cladribine, doxifluridine, hydroxycarbamide, mercaptopurine, and the like.

Examples of microtubule inhibitors include alkaloid-based anticancer agents, such as vincristine, and taxane-based anticancer agents, such as docetaxel and paclitaxel.

Examples of antibiotic anticancer agents include mitomycin C, doxorubicin, epirubicin, daunorubicin, bleomycin, actinomycin D, aclarubicin, idarubicin, pirarubicin, peplomycin, mitoxantrone, amrubicin, zinostatin stimalamer, and the like.

Examples of topoisomerase inhibitors include CPT-11, irinotecan, and nogitecan, which have topoisomerase I inhibitory activity; and etoposide and sobuzoxane, which have topoisomerase II inhibitory activity.

Examples of platinum agents include cisplatin, nedaplatin, oxaliplatin, carboplatin, and the like.

Examples of hormonal agents include dexamethasone, finasteride, tamoxifen, astrozole, exemestane, ethinyl estradiol, chlormadinone, goserelin, bicalutamide, flutamide, prednisolone, leuprorelin, letrozole, estramustine, toremifene, fosfestrol, mitotane, methyltestosterone, medroxyprogesterone, mepitiostane, and the like.

Examples of biologics include interferon-α, -β, and -γ, interleukin 2, ubenimex, dried BCG, extracellular toxins, and the like. Specific examples of extracellular toxins include exotoxins (proteins) produced by the bacterium *Pseudomonas* exotoxin (PE). PE has the enzyme activity of NAD+-diphthamide-ADP-ribosyl transferase, which inhibits protein synthesis and exhibits strong toxicity. So far, PE conjugated to an antibody called CD22 antibody has been approved as an anticancer agent.

Examples of molecular target drugs include rituximab, alemtuzumab, trastuzumab, cetuximab, panitumumab, imatinib, dasatinib, nilotinib, gefitinib, erlotinib, temsirolimus, bevacizumab, VEGF trap, sunitinib, sorafenib, tositumomab, bortezomib, gemtuzumab ozogamicin, ibritumomab ozogamicin, ibritumomab tiuxetan, tamibarotene, tretinoin, and the like. In addition to the molecular target drugs specified here, other examples include immune checkpoint inhibitors, such as anti-PD-1 antibodies (e.g., nivolumab and pembrolizumab), anti-PD-L1 antibodies (e.g., atezolizumab, durvalumab, avelumab, and cemiplimab), and anti-CTLA-4 antibodies (e.g., ipilimumab and tremelimumab); inhibitors targeting angiogenesis, such as human epidermal growth factor receptor 2 inhibitors, epidermal growth factor receptor inhibitors, Bcr-Abl tyrosine kinase inhibitors, epidermal growth factor tyrosine kinase inhibitors, mTOR inhibitors, and vascular endothelial growth factor receptor 2 inhibitors (α-VEGFR-2 antibodies); various tyrosine kinase inhibitors, such as MAP kinase inhibitors; inhibitors targeting cytokines, proteasome inhibitors, antibody-anticancer drug conjugates, and other molecular target drugs. These inhibitors also include antibodies.

Nucleic acid drugs are active pharmaceutical ingredients that are nucleic acids, and are not particularly limited in that respect.

The content of other substances is, for example, 0 to 10000 parts by mass, 0 to 1000 parts by mass, 0 to 500 parts by mass, 0 to 100 parts by mass, 0 to 50 parts by mass, or 0 to 10 parts by mass, based on 100 parts by mass of the sum of the compound of formula (1) and the modified polysaccharide.

In a preferred embodiment, the complex of the present invention can be obtained in a dissolved state in water or a solvent with a smaller amount of organic solvent (e.g., a solvent with an organic solvent content of 1 mass % or less, 0.5 mass % or less, 0.2 mass % or less, 0.1 mass % or less, 0.01 mass % or less, or 0.001 mass % or less, per 100 mass % of the solvent). The complex of the present invention can preferably be in a dissolved state in water (in the form of an aqueous solution).

In the complex solution of the present invention (particularly a solution using the above solvent), the concentration of the compound of formula (1) is preferably 0.1 mg/mL or more, 0.2 mg/mL or more, 0.4 mg/mL or more, 0.6 mg/mL or more, 0.8 mg/mL or more, or 1.0 mg/mL or more. The upper limit of the concentration is not particularly limited, and is, for example, 10 mg/mL, 6 mg/mL, 4 mg/mL, or 2 mg/mL. According to the present invention, it is possible to obtain a solution containing the compound of formula (1), which is poorly soluble in water, at a relatively high concentration as described above.

In the complex solution of the present invention (particularly a solution using the above solvent), the concentration of the modified polysaccharide is preferably 1 to 30 mg/mL, 2 to 25 mg/mL, 4 to 20 mg/mL, 6 to 15 mg/mL, or 8 to 12 mg/mL.

The complex of the present invention can be produced by, for example, stirring a solution containing the compound of formula (1) and a modified polysaccharide (solution 1) at a relatively low temperature. This method is excellent in terms of improving the concentration of the compound of formula (1) in the complex of the present invention.

The solvent of solution 1 contains water. To dissolve the compound of formula (1), the solvent of solution 1 preferably contains an organic solvent. The organic solvent is not particularly limited as long as it is a solvent that can dissolve the compound of formula (1) and is compatible with water. Preferably, dimethyl sulfoxide or N,N-dimethylformamide can be used. The content of water in the solvent of solution 1 is preferably 90.0 to 100 v/v %, more preferably 95.0 to 99.5 v/v %, even more preferably 97.0 to 99.0 v/v % or more, and still even more preferably 97.5 to 98.5 v/v % or more. The content of the organic solvent in the solvent of solution 1 is preferably 0 to 10 v/v %, more preferably 0.5 to 5.0 v/v %, even more preferably 1.0 to 3.0 v/v %, and still even more preferably 1.5 to 2.5 v/v %.

The concentration of the compound of formula (1) in solution 1 is preferably 0.05 to 0.8 mg/mL, and more preferably 0.1 to 0.4 mg/mL. The concentration of the modified polysaccharide in solution 1 is preferably 0.2 to 4 mg/mL, and more preferably 0.5 to 3 mg/mL. The mass ratio of the modified polysaccharide to the compound of formula (1) in solution 1 (mass of modified polysaccharide/mass of compound) is preferably 1 to 20, more preferably 2 to 10, and even more preferably 3 to 7.

Solution 1 can be preferably obtained by dissolving the compound of formula (1) and a modified polysaccharide in an organic solvent, and then adding water.

The water used for solution 1 may contain a buffer, such as a phosphate buffer.

The temperature of solution 1 during stirring is preferably 1 to 10° C., and more preferably 2 to 6° C. The stirring time of solution 1 is preferably 4 to 24 hours, and more preferably 6 to 16 hours. As a result of stirring under these conditions, a complex with a more uniform shape and particle size can be obtained.

After stirring, the resultant can be subjected to purification treatment, if necessary. Examples of the purification treatment include filter filtration, ultrafiltration, and the like. Preferably, ultrafiltration can be used for concentration and removal of the organic solvent. This process makes it possible to adjust the mass ratio of the modified polysaccharide to the compound of formula (1) described above.

2. Use

The complex of the present invention has an anticancer effect and a macrophage polarization effect (polarization from M2-like to M1-like). Therefore, the complex of the present invention can be used as an active ingredient of drugs, reagents, etc. (also referred to as "the drug of the present invention" in the present specification), and specifically used as an active ingredient of cancer therapeutic agents, macrophage (preferably TAM) polarizing agents, etc.

The drug of the present invention is not particularly limited as long as it comprises the complex of the present invention. The drug of the present invention may further contain other components, if necessary. The other components are not particularly limited as long as they are pharmaceutically acceptable components. Examples of the other components include additives in addition to components with pharmacological effects.

Examples of additives include bases, carriers, solvents, dispersants, emulsifiers, buffers, stabilizers, excipients, binders, disintegrators, lubricants, thickeners, moisturizers, coloring agents, flavoring agents, chelating agents, and the like.

In addition to the complex of the present invention, the drug of the present invention may contain the other substances mentioned above that can be contained in the complex of the present invention (e.g., drugs, such as adjuvants, cancer antigens, anticancer agents, and nucleic acid drugs). Further, the drug of the present invention may be used in combination with the other substances mentioned above that can be contained in the complex of the present invention (e.g., drugs, such as adjuvants, cancer antigens, anticancer agents, and nucleic acid drugs). In particular, as shown in the Examples below (Test Example 10) showing effects regarding the combined use with an anti-PD-1 antibody, the combined use with an immune checkpoint inhibitor is useful in terms of antitumor effects. Examples include immune checkpoint inhibitors, such as anti-PD-1 antibodies (e.g., nivolumab and pembrolizumab), anti-PD-L1 antibodies (e.g., atezolizumab, durvalumab, avelumab, and cemiplimab), and anti-CTLA-4 antibodies (e.g., ipilimumab and tremelimumab).

The usage mode of the drug of the present invention is not particularly limited, and a suitable usage mode can be used depending on the type thereof. The drug of the present invention can be used, for example, in vitro (e.g., added to a medium of cultured cells) or in vivo (e.g., administered to an animal) depending on the use thereof.

The application object of the drug of the present invention is not particularly limited. Examples of mammals include humans, monkeys, mice, rats, dogs, cats, rabbits, pigs, horses, cows, sheep, goats, deer, and the like. Further, examples of cells include animal cells and the like. The type of cell is also not particularly limited, and examples include immune cells (preferably macrophages), blood cells, hematopoietic stem cells/progenitor cells, gametes (sperm and egg), fibroblasts, epithelial cells, vascular endothelial cells, neurons, hepatocytes, keratinocytes, muscle cells, epidermal cells, endocrine cells, ES cells, iPS cells, tissue stem cells, cancer cells, and the like. Preferred among these are macrophages, and particularly preferred are TAMs.

When the drug of the present invention targets cancer, the target cancer is not particularly limited. Examples include leukemia (including chronic lymphocytic leukemia and acute lymphocytic leukemia), lymphoma (including non-Hodgkin's lymphoma, Hodgkin's lymphoma, T-cell lymphoma, B-cell lymphoma, Berkit's lymphoma, malignant lymphoma, diffuse lymphoma, and follicular lymphoma), myeloma (including multiple myeloma), breast cancer, colon cancer, kidney cancer, gastric cancer, ovarian cancer, pancreatic cancer, cervical cancer, endometrial cancer, esophageal cancer, liver cancer, head and neck squamous epithelial cancer, skin cancer, malignant melanoma, urinary tract cancer, prostate cancer, villous cancer, pharyngeal cancer, laryngeal cancer, thecoma, male germinoma, endometrial hyperplasia, endometriosis, embryoma, fibrosarcoma, Kaposi sarcoma, hemangioma, cavernous hemangioma, hemangioblastoma, retinoblastoma, astrocytoma, neurofibroma, oligodendroglioma, medulloblastoma, neuroblastoma, glioma, rhabdomyosarcoma, medulloblastoma, osteogenic sarcoma, leiomyosarcoma, thyroid sarcoma, Wilms tumor, and the like.

The drug of the present invention can have any dosage form, and examples include oral dosage forms, such as tablets (including orally disintegrating tablets, chewable tablets, foaming tablets, troches, jelly drops, etc.), pills, granules, subtle granules, powders, hard capsules, soft capsules, dry syrups, liquids (including drinkable preparations, suspensions, and syrups), and jellies; and parenteral dosage forms, such as injectable preparations (e.g., drip injections (intravenous drip injections etc.), intravenous injections, intramuscular injections, subcutaneous injections, and intradermal injections), external preparations (e.g., ointments, poultices, and lotions), suppositories, inhalants, eye drops, eye ointments, nasal drops, ear drops, and liposome preparations.

The route of administration of the drug of the present invention is not particularly limited as long as desired effects are obtained. Examples include enteral administration, such as oral, tube feeding, and enema administration; parenteral administration, such as intravenous, intraarterial, intramuscular, intracardiac, subcutaneous, intradermal, and intraperitoneal administration; and the like.

The content of the active ingredient (the complex of the present invention) in the drug of the present invention varies depending on the usage mode, application object, the state of the application object, etc., and is not limited. For example, the content of the active ingredient is 0.0001 to 100 wt. %, and preferably 0.001 to 50 wt. %.

The dose of the drug of the present invention when administered to an animal is not particularly limited as long as it is an effective amount for expressing drug effects. In the case of oral administration, the weight of the active ingredient is generally 0.1 to 1000 mg/kg body weight per day, and preferably 0.5 to 500 mg/kg body weight per day. In the case of parenteral administration, the weight of the active ingredient is 0.01 to 100 mg/kg body weight per day, and preferably 0.05 to 50 mg/kg body weight per day. The above dose can be suitably increased or decreased according to the age, pathological conditions, symptoms, etc.

EXAMPLES

The present invention is described in detail below based on Examples; however, the present invention is not limited to these Examples.

Preparation Example 1. Preparation of Cholesterol-Modified Pullulan

According to a previously reported document (Macromolecules 1993, 23, 3062-3068), cholesterol-modified pullulan (hereinafter, CHP) was produced by introducing 1.2 cholesterols per 100 monosaccharides to pullulan having a weight average molecular weight of 100,000.

Example 1. Examination of Encapsulation of Various TLR7 and TLR8 Agonists in CHP Nanogel Nine TLR7 and TLR8 agonists (Telratolimod, Motolimod, Vesatolimod, Resiquimod, Imiquimod, CL075, CU-CPT17e, CU-CPT9a, and PF-4878691) were examined for whether they could be encapsulated in CHP nanogel. CHP was dissolved in a 6 M urea solution in PBS(−), and a compound solution was added thereto. Then, stepwise dialysis was performed against PBS(−).

Results

Of the nine compounds, only one (Telratolimod) could be stably encapsulated in the CHP nanogel and formed into a solution.

Consideration

The Telratolimod concentration of the nanogel preparation obtained in Example 1 was as low as 0.112 mg/ml. Further improvement of the Telratolimod concentration was expected to demonstrate sufficient efficacy.

Example 2. Preparation of Telratolimod-Encapsulated CHP Nanogel

Telratolimod-encapsulated CHP nanogel (hereinafter, CHP:Telratolimod) was prepared in the following manner.

160 mg of CHP 80K (NOF Corporation) and 32 mg of Telratolimod (ACHEMBLOCK) were mixed and dissolved in 3.2 mL of N,N-dimethylformamide (DMF). This DMF solution was added to 160 mL of PBS and stirred at 4° C. overnight. The filtrate was passed through a 0.8 μm filter, and concentrated and purified using TFF (Pall, MWCO; 30K) to remove the DMF. After collection, the resultant was passed through a 0.45 μm filter to obtain a CHP:Telratolimod solution (scattering intensity average particle size: 149 nm, ELSZ-2000ZS, Otsuka Electronics Co., Ltd.). Using a Telratolimod standard sample, a calibration curve was prepared by HPLC (column: YMC-Pack C4, 150×2.0 mm I.D. S-3 μm, 12 nm, flow rate: 0.3 mL/min 60% B line, A line: 0.1% FA in $H_2O$, B line: 0.1% FA in $CH_3CN$), and the Telratolimod concentration in the CHP:Telratolimod solution was calculated by decomposing CHP in an aqueous solution of sodium periodate, and then quantifying the resulting aldehyde groups with Schiff's reagent, thereby calculating the CHP concentration (CHP: 10.2 mg/mL, Telratolimod: 1.17 mg/mL).

Consideration

The Telratolimod concentration in the nanogel preparation obtained by the newly discovered method in Example 2 was 1.17 mg/ml, which was about 10 times higher than that obtained by the previous method. By forming the poorly soluble drug into a nanogel preparation by this method, the drug concentration was successfully improved. In the following Test Examples 1 to 17, the preparation prepared in Example 2 was used.

Test Example 1. Preparation of Human Peripheral Blood-Derived TAMs

Human peripheral blood-derived CD14-positive monocytes that had been cryopreserved in advance were awake and seeded in a 24-well tissue culture plate at $2\times10^5$ cells/well in 500 μL of basal medium (RPMI, 10% fetal bovine serum, 50 ng/mL M-CSF) and cultured for 3 days in a 37° C., 5% $CO_2$ incubator, after which 500 μL of basal medium was further added, and the cells were cultured for 3 days. The medium was then replaced with 500 μL of TAM differentiation induction medium prepared by adding 10% fetal bovine serum, 50 ng/mL IL-4, 50 ng/mL IL-6, 50 ng/mL IL-10, 50 ng/mL IL-13, and 5% human AB type male donor defibrinated serum (Veritas) to a separately prepared culture supernatant of human cancer cells, and the cells were cultured for 2 days.

Test Example 2. Polarization Test of Human Peripheral Blood-Derived TAMs

A Telratolimod solution or CHP:Telratolimod solution adjusted to a final concentration of 30 μM in terms of Telratolimod was added to the TAM prepared in Test Example 1, followed by incubation for 2 days, and TNF-α in the culture supernatant was measured by ELISA (BioLegend). The control was supplemented with only medium.

Results

The results are shown in Table 1. Compared to Telratolimod, CHP:Telratolimod showed higher TNF-α production. This suggests that the encapsulation of Telratolimod in CHP nanogel allows Telratolimod to be more efficiently taken up by TAMs, causing their polarization into M1-like macrophages, resulting in higher TNF-α production.

TABLE 1

| Test drug | | TNF-α (pg/mL) |
|---|---|---|
| Control | Medium only | Below detection limit |
| Telratolimod | 30 μM | 700 |
| CHP:Telratolimod | 30 μM | 1300 |

Test Example 3. Cancer Cell Phagocytosis Test of Human Peripheral Blood-Derived TAMs HeLa cells were labeled with fluorescent label 1 (CellTracker Green CMTPX Dye, ThermoFisher) for 30 minutes, then washed twice with PBS(−), and cultured overnight in medium (RPMI supplemented with 10% fetal bovine serum) containing 1.25 μM doxorubicin.

TAMs were prepared in the same manner as in Test Example 1, and Telratolimod or CHP:Telratolimod adjusted to a final concentration of 10 μM in terms of Telratolimod was added to the basal medium, followed by incubation for 2 days. After labeling with fluorescent labeling agent 2 (CellTracker Red CMTPX Dye, ThermoFisher) for 30 minutes, the cells were washed twice with PBS(−). The doxorubicin-treated HeLa cells were added at a half ratio to the TAMs and co-cultured overnight. The cells were then harvested, and the number of cells co-positive for fluorescent labels 1 and 2 was determined by flow cytometry. The control was supplemented with only medium.

Results

The results are shown in Table 2. Compared to Telratolimod, CHP:Telratolimod enhanced phagocytic activity against the HeLa cancer cells. It is shown that the encapsulation of Telratolimod in CHP nanogel allows Telratolimod to be more efficiently taken up by TAMs, causing their polarization into M1-like macrophages, resulting in enhanced phagocytic activity.

TABLE 2

| Test drug | | Phagocytosis rate |
|---|---|---|
| Control | Medium only | 5.1% |
| Telratolimod | 10 μM | 5.5% |
| CHP:Telratolimod | 10 μM | 12.6% |

Test Example 4. Measurement of Blood Concentration Changes in Mouse Allogeneic Tumor Transplantation Model A mouse allogeneic tumor transplantation model was prepared by intradermally administering $10^6$ cells of the mouse colon cancer cell line MC38 into the dorsal skin of mice (C57BL/6JJmsSlc, female). Mice on day 7 after cell administration were used. 84.5 μg of CHP:Telratolimod prepared in Example 2 or Telratolimod dissolved in a solubilizing solvent (17.1% polyethylene glycol 300, 4.3% Tween 80, and 8.6% polyoxyethylene hydrogenated castor oil) was administered via tail vein injection, and changes in the concentration of Telratolimod in the blood were measured. Blood was collected from 5 mice per group. After each test drug was administered via tail vein injection, 80 μL of isopropyl alcohol was added to 20 μL of serum collected after 1 minute, 30 minutes, 1 hour, 2 hours, and 6 hours, and bead crushing was performed for 1 minute using a 5 mm diameter stainless steel ball. Further, 400 μL of an 80% isopropyl alcohol and 20% acetonitrile solution was added and mixed, followed by sonication for 3 minutes, and centrifugation at 12000 g for 5 minutes to collect the supernatant. The collected supernatant was analyzed by LS-MS/MS to measure the Telratolimod concentration. To create a calibration curve, a standard solution of Telratolimod was prepared in 1.17 mg/mL DMSO solution, and a dilution series of 10, 20, 100, 200, 1000, and 2000 times was prepared and then diluted 10 times with fetal bovine serum, which was used to perform correction using cabozantinib (Selleck) as an internal standard.

Results

The results are shown in FIG. 1. The blood concentration of Telratolimod rapidly decreased within 30 minutes after administration, whereas Telratolimod encapsulated in CHP nanogel was more persistent in blood, confirming that the blood half-life was extended by 4 times or more.

Test Example 5. Measurement of Intratumoral Telratolimod Concentration in Mouse Allogeneic Tumor Transplantation Model Using a mouse allograft model prepared in the same manner as in Test Example 4, the CHP:Telratolimod solution containing 84.5 μg of Telratolimod prepared in Example 2, and the Telratolimod solution prepared in Test Example 4 were each administered via tail vein injection. The tumors were excised 1 hour later, and the concentration of Telratolimod in the tumors was measured. 5 mice were used for each group. 80 μL of isopropyl alcohol was added to 20 μg of excised tumor fragments, and bead crushing was performed for 1 minute using a 5 mm diameter stainless steel ball. Subsequent treatment was carried out in the same manner as in Test Example 4.

Results

Figure 2:
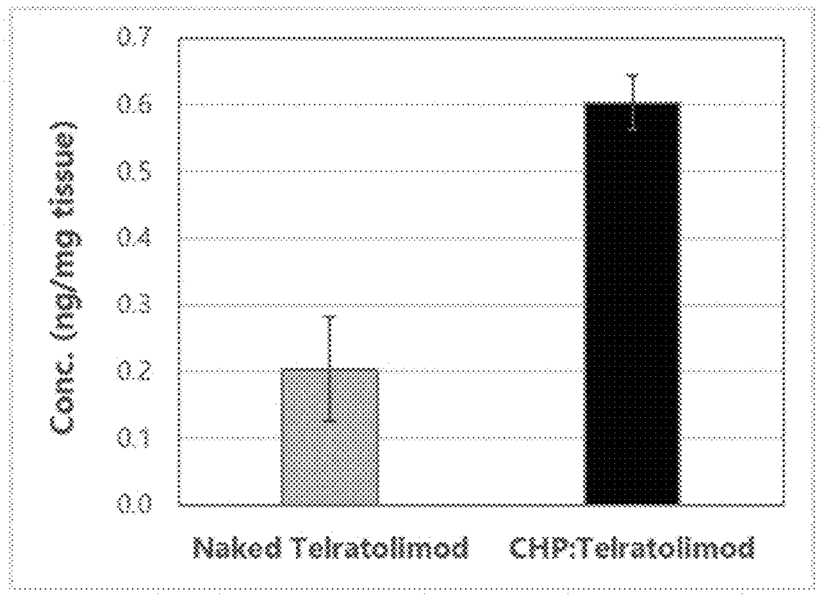
FIG. 2 shows the results of Test Example 5. The vertical axis indicates the concentration of Telratolimod contained in the tumor, and the horizontal axis indicates the test drugs added.

The results are shown in FIG. 2. Encapsulation in CHP nanogel increased the intratumoral accumulation of Telratolimod approximately 3 times.

Test Example 6. Antitumor Evaluation in Mouse Allogeneic Tumor Transplantation Model (1)

An MC38 mouse allogeneic tumor transplantation model was prepared in the same manner as in Test Example 4. On days 7, 9, 11, 14, 16, and 18 after cell transplantation, the CHP:Telratolimod solution prepared in Example 2 and the Telratolimod solution prepared in Test Example 4 were each administered via tail vein injection to 5 mice per group (amount of Telratolimod: 84.5 μg). Tumor sizes were measured on days 7, 9, 11, 14, 16, 18, and 19. The tumor volume was calculated by (long axis×short axis×short axis)/2. As a negative control, the same solution as the solvent for each drug was administered. “Vehicle 1” refers to the solubilizing solvent of Test Example 4, and “Vehicle 2” refers to PBS(−).

Results

Figure 3:
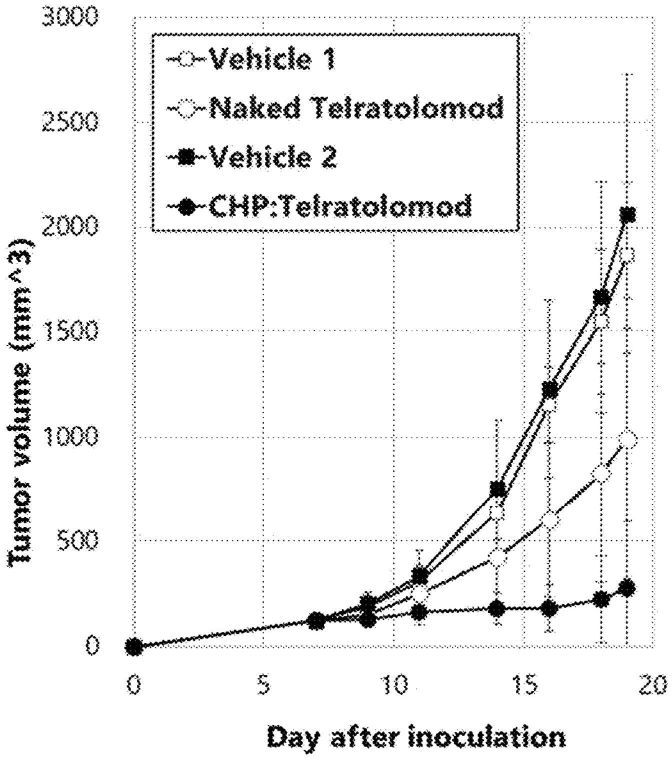
FIG. 3 shows the results of Test Example 6. The vertical axis indicates the tumor volume, and the horizontal axis indicates the number of days since the day cancer cells were implanted intradermally, which was regarded as day 0. The legend indicates test drugs.

The results are shown in FIG. 3. In the CHP:Telratolimod-treated group, the tumor volume remained almost unchanged from the start of drug administration, and on day 19, the growth inhibition was 92% compared to the solvent control. On the other hand, in the Telratolimod-treated group, the growth inhibition was 49% compared to the solvent control. These results indicate that the encapsulation of Telratolimod in CHP nanogel dramatically enhanced the antitumor effect of Telratolimod.

Test Example 7. Evaluation of TAM Polarization in Mouse Allogeneic Tumor Transplantation Model An MC38 mouse allogeneic tumor transplantation model was prepared in the same manner as in Test Example 6, and on days 7, 9, and 11 after cell transplantation, the CHP: Telratolimod solution prepared in Example 2 and the Telratolimod solution prepared in Test Example 4 were each administered via tail vein injection to 5 mice per group (amount of Telratolimod: 84.5 μg). One day after the final administration, the tumors were excised, and macrophages infiltrating into the tumors were measured by flow cytometry. Significance tests were performed using one-way ANOVA (*P<0.05, P<0.01, *P<0.001, ****P<0.0001).

Results

Figure 4:
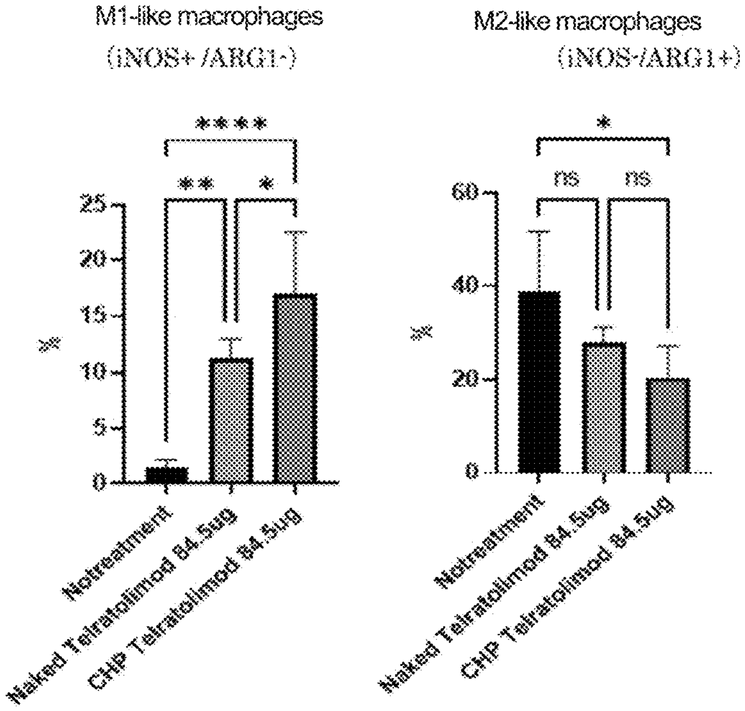
FIG. 4 shows the results of Test Example 7. The graph on the left shows the measurement results of M1-like macrophages (vertical axis), and the graph on the right shows the measurement results of M2-like macrophages (vertical axis). The horizontal axis indicates the test drugs added. "No treatment" indicates the case where no test drug was added.

The results are shown in FIG. 4. In both the Telratolimod-treated group and the CHP:Telratolimod-treated group, the expression of iNOS, which is an M1-like macrophage marker, was significantly increased. In the CHP:Telratolimod-treated group, the iNOS level was significantly higher than the Telratolimod-treated group. Further, the expression of ARG1, which is an M2-like macrophage marker, tended to decrease in both the Telratolimod-treated group and the CHP:Telratolimod-treated group, but significantly decreased only in the CHP:Telratolimod-treated group. These results indicate that more M2-like macrophages in tumors polarized to M1-like macrophages in the CHP:Telratolimod-treated group than in the Telratolimod-treated group.

Test Example 8. Evaluation of Cytokine Release in Mouse Allogeneic Tumor Transplantation Model The allograft model mice used were 10 days after $10^6$ cells of the mouse colorectal cancer cell line MC38 were administered intradermally into the dorsal skin of mice (C57BL/6JJmsSlc, female). The Telratolimod solution prepared in Test Example 4 and the CHP:Telratolimod solution prepared in Example 2 were each administered (amount of Telratolimod: 84.5 μg) via tail vein injection to 5 mice per group, and blood was collected after 2 hours. The serum was obtained by centrifugation, and changes in the amount of cytokines were measured using LEGENDplex Mouse Inflammation Panel (BioLegend). Significance tests were performed using one-way ANOVA (*P<0.05, P<0.01, *P<0.001, ****P<0.0001).

Results

Figure 5:
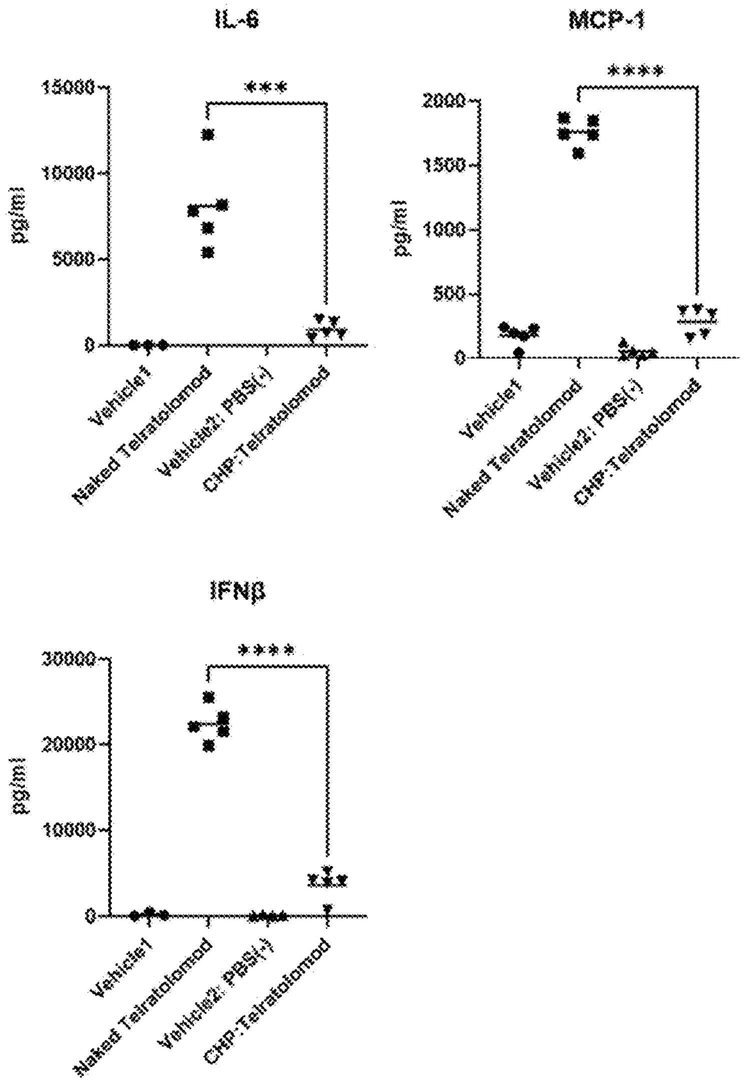
FIG. 5 shows the results of Test Example 8. Graphical information shows the cytokines measured. The vertical axis indicates the cytokine concentration in serum, and the horizontal axis indicates the test drugs administered.

The results are shown in FIG. 5. In the Telratolimod solution-treated group, rapid increases in IL-6, MCP-1, and IFN-β were observed, suggesting the possibility of cytokine release syndrome. On the other hand, these increases were significantly reduced in the CHP:Telratolimod-treated group, indicating that cytokine release syndrome was suppressed.

Test Example 9. Blood Test in Mouse Allogeneic Tumor Transplantation Model $10^6$ cells of the mouse colorectal cancer cell line MC38 were administered intradermally into the dorsal skin of mice (C57BL/6JJmsSlc, female). After 7 days, 9 days, and 11 days, the Telratolimod solution prepared in Test Example 4 and the CHP:Telratolimod solution prepared in Example 2 were each administered (amount of Telratolimod: 84.5 μg) via tail vein injection to 5 mice per group. One day after the final administration, blood was collected, and changes in red blood cell and reticulocyte counts were measured. Significance tests were performed using one-way ANOVA (*P<0.05, P<0.01, *P<0.001, ****P<0.0001).

Results

Figure 6:
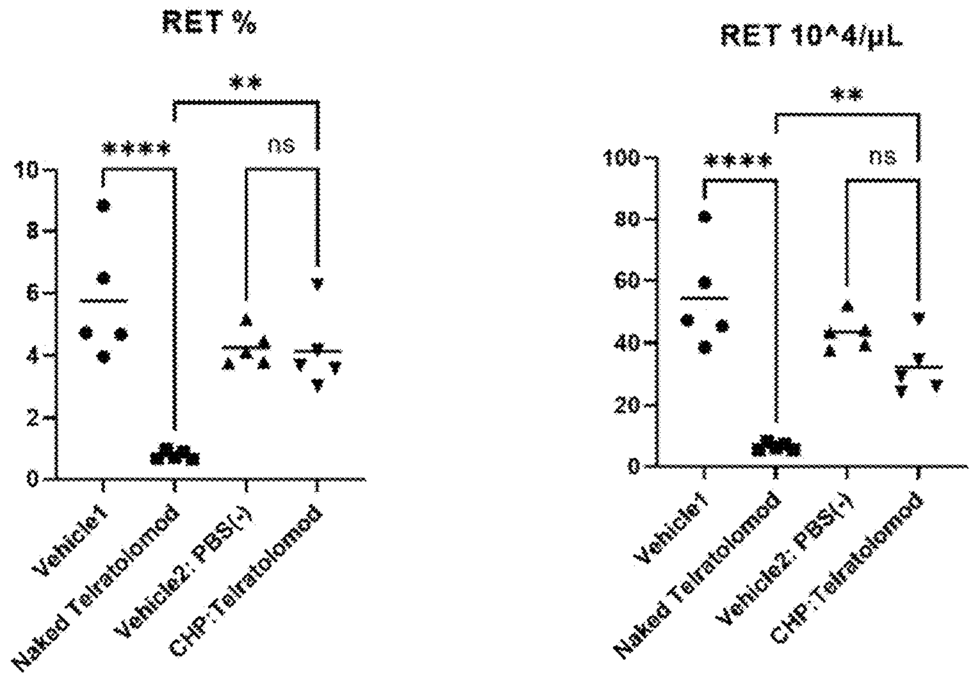
FIG. 6 shows the results of Test Example 9. RET stands for reticulocytes. The graph on the left shows the measurement results of the ratio of the reticulocyte count to the total red blood cell count (vertical axis: %), and the graph on the right shows the measurement results of the blood concentration of reticulocytes (vertical axis: $\times 10^4/\mu L$).

The results are shown in FIG. 6. A significant decrease in reticulocytes was observed in the Telratolimod solution-treated group. On the other hand, this was not observed in the CHP:Telratolimod solution-treated group. Reticulocytes are an indicator of the production of red blood cells in the bone marrow, and toxicity to the bone marrow was suggested in the Telratolimod solution-treated group. On the other hand, it was significantly reduced in the CHP:Telratolimod solution-treated group, suggesting that encapsulation in CHP nanogel does not cause bone marrow suppression.

Test Example 10. Antitumor Evaluation in Mouse Allogeneic Tumor Transplantation Model (2)

A mouse allogeneic tumor transplantation model was prepared by intradermally administering $10^6$ cells of the mouse colorectal cancer cell line CT26 into the dorsal skin of mice (BALB/cCrSlc, female). On days 7, 9, 11, 14, 16, and 18 after cell transplantation, the CHP:Telratolimod solution prepared in Example 2 and the Telratolimod solution prepared in Test Example 4 were each administered via tail vein injection, and on days 7, 11, 14, and 18 after cell transplantation, an anti-PD-1 antibody (RMP1-14, Bio X Cell) solution was administered intraperitoneally, to 5 mice per group (amount of Telratolimod: 42 μg, amount of anti-PD-1 antibody: 100 μg). One group received a combination of the CHP:Telratolimod solution and the anti-PD-1 antibody. Tumor sizes were measured on days 7, 9, 11, 14, 16, 18, and 21. The tumor volume was calculated by (long axis×short axis×short axis)/2. The negative control is an untreated group.

Results

Figure 7:
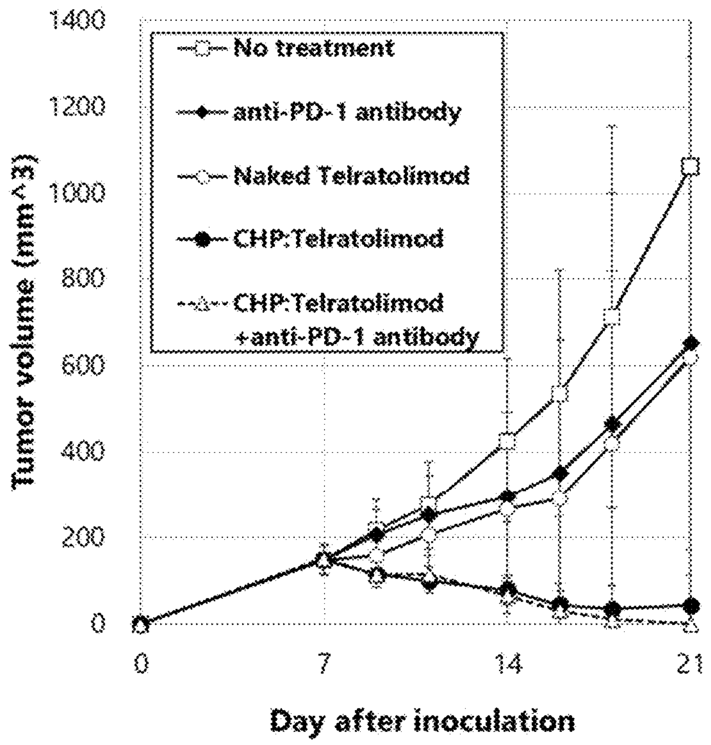
FIG. 7 shows the results of Test Example 10. The vertical axis indicates the tumor volume, and the horizontal axis indicates the number of days since the day cancer cells were implanted intradermally, which was regarded as day 0. The legend indicates test drugs.

The results are shown in FIG. 7. In the CHP:Telratolimod-treated group, the tumors regressed from the start of drug administration. On the other hand, the antitumor effect of the Telratolimod-treated group was limited, indicating that encapsulation in CHP nanogel dramatically enhanced the antitumor effect of Telratolimod. The antitumor effect of the anti-PD-1 antibody was also limited; however, when the anti-PD-1 antibody was combined with CHP:Telratolimod, the tumor completely disappeared. These results indicate that the combination with CHP:Telratolimod may be expected to have a strong antitumor effect in cancers in which the antitumor effect of the anti-PD-1 antibody is limited (so-called cold tumors).

Test Example 11. Preparation of Human Peripheral Blood-Derived M2-Like Macrophages Human peripheral blood-derived CD14-positive monocytes that had been cryopreserved in advance were awake and seeded in a 24-well tissue culture plate at $2\times10^5$ cells/well in 500 μL of basal medium (RPMI, 10% fetal bovine serum, 50 ng/mL M-CSF) and cultured for 3 days in a 37° C., 5% $CO_2$ incubator, after which 500 μL of basal medium was further added, and the cells were cultured for 3 days. The medium was then replaced with 500 μL of M2-like macrophage differentiation induction medium prepared by adding 50 ng/mL IL-4, 50 ng/mL IL-6, 50 ng/mL IL-10, and 50 ng/mL IL-13 to the basal medium, and the cells were cultured for 2 days.

Test Example 12. Polarization Test of Human Peripheral Blood-Derived M2-Like Macrophages A Telratolimod solution or CHP:Telratolimod solution adjusted to a final concentration of 3 μM in terms of Telratolimod was added to the M2-like macrophages prepared in Test Example 11, followed by incubation for 1 day, and TNF-α, IL-1β, IL-6, IL-12p40 (p40 subunit of IL-12), IL-23, and CXCL10 in the culture supernatant were measured using a flow cytometry bead assay kit (LEGENDplex™, BioLegend). The control was supplemented with only medium.

Results

The results are shown in Table 3. Compared to Telratolimod, CHP:Telratolimod showed higher production of TNF-α, IL-1β, IL-6, IL-12p40, IL-23, and CXCL10. This suggests that the encapsulation of Telratolimod in CHP nanogel allows Telratolimod to be more efficiently taken up by M2-like macrophages, causing their polarization into M1-like macrophages, resulting in higher production of pro-inflammatory cytokines (TNF-α, IL-1β, IL-6, IL-12 (p40 subunit), IL-23, and CXCL10) produced by M1-like macrophages.

TABLE 3

| Test drug | | TNF-α (pg/mL) | IL-1β (pg/mL) | IL-6 (pg/mL) |
|---|---|---|---|---|
| Control | Medium only | 6.5 ± 1.6 | 3.5 ± 0.17 | 1900 ± 260 |
| Telratolimod | 3 μM | 40 ± 7.3 | 2.3 ± 0.64 | 3100 ± 380 |
| CHP:Telratolimod | 3 μM | 270 ± 45 | 6.8 ± 1.6 | 9100 ± 100 |
| **Test drug** | | **IL-12p40 (pg/mL)** | **IL-23 (pg/mL)** | **CXCL10 (pg/mL)** |
| Control | Medium only | 100 ± 31 | 1.7 ± 0.46 | 230 ± 42 |
| Telratolimod | 3 μM | 59 ± 22 | 1.4 ± 0.35 | 140 ± 20 |
| CHP:Telratolimod | 3 μM | 250 ± 24 | 4.9 ± 0.32 | 380 ± 34 |

Test Example 13. Cancer Cell Phagocytosis Test of Human Peripheral Blood-Derived M2-Like Macrophages HeLa cells were labeled with fluorescent label 1 (CellTracker Green CMTPX Dye, ThermoFisher) for 30 minutes, then washed twice with PBS(−), and cultured overnight in medium (RPMI supplemented with 10% fetal bovine serum) containing 2.5 μM doxorubicin.

Telratolimod or CHP:Telratolimod adjusted to a final concentration of 10 μM in terms of Telratolimod was added to the basal medium, and the M2-like macrophages prepared in Test Example 11 were incubated for 1 day. After labeling with fluorescent labeling agent 2 (CellTracker Red CMTPX Dye, ThermoFisher) for 30 minutes, the cells were washed twice with PBS(−). The HeLa cells were added at a half ratio to the M2-like macrophages and co-cultured overnight. The cells were then harvested, and the number of cells co-positive for fluorescent labels 1 and 2 was determined by flow cytometry. The control was supplemented with only medium.

Results

The results are shown in Table 4. Compared to Telratolimod, CHP:Telratolimod enhanced phagocytic activity against the HeLa cancer cells. It is shown that the encapsulation of Telratolimod in CHP nanogel allows Telratolimod to be more efficiently taken up by TAMs, causing their polarization into M1-like macrophages, resulting in enhanced phagocytic activity.

TABLE 4

| Test drug | | Phagocytosis rate |
|---|---|---|
| Control | Medium only | 9.3% |
| Telratolimod | 10 μM | 9.7% |
| CHP:Telratolimod | 10 μM | 19.5% |

Test Example 14. Antitumor Evaluation in Mouse Allogeneic Tumor Transplantation Model (3)

Of the CHP:Telratolimod-treated group in Test Example 10, mice with complete tumor regression on day 21 (n=4) were continued to be housed, and it was confirmed until day 96 that tumors did not relapse in all cases. Subsequently, on day 97, $10^6$ cells of the mouse colorectal cancer cell line CT26 were implanted intradermally into the dorsal skin on the side opposite to the cancer cell line implanted in Test Example 10, and tumor growth was measured until day 120. As a control, 5 mice (BALB/cCrSlc, female) of the same age that had not previously been implanted with the CT26 cancer cell line were prepared. $10^6$ cells of the CT26 cancer cell line were implanted intradermally into the dorsal skin of the mice, and tumor growth was measured.

Results

Figure 8:
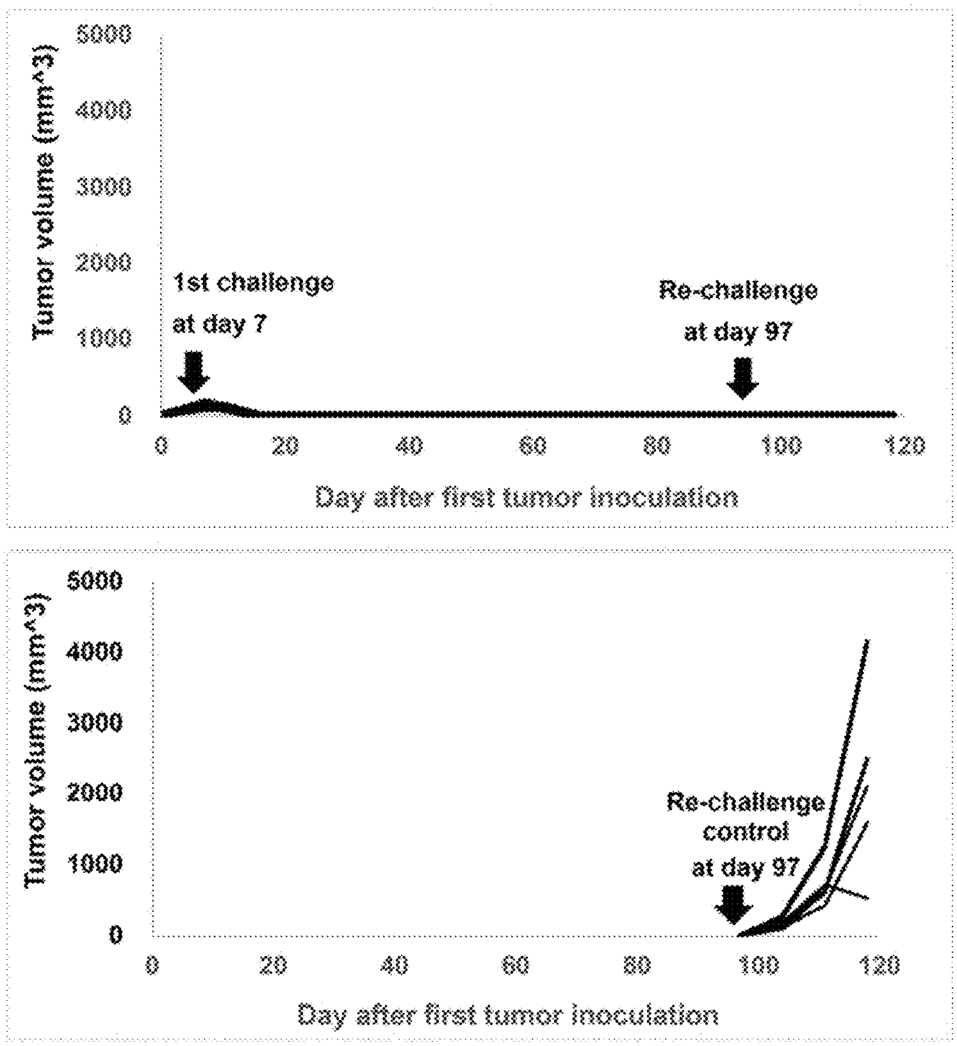
FIG. 8 shows the results of Test Example 11. The vertical axis indicates the tumor volume, and the horizontal axis indicates the number of days elapsed.

The results are shown in FIG. 8. As the control, the mice of the same age that had not previously been implanted with the CT26 cancer cell line showed tumor growth in all cases (FIG. 8, bottom). On the other hand, in the mice that showed complete regression after the first transplantation of cancer cells, the tumor did not develop in all cases, and the transplanted cancer cells were completely rejected (FIG. 8, top). These results indicate that CHP:Telratolimod induces immune memory against cancer cells, suggesting that remission achieved with CHP:Telratolimod may prevent relapse.

Test Example 15. Analysis of Tumor-Infiltrating CD8-Positive T Cells and Natural Killer Cells (NK Cells) in Mouse Allogeneic Tumor Transplantation Model An MC38 mouse allogeneic tumor transplantation model was prepared in the same manner as in Test Example 6. On days 7 and 9 after cell transplantation, the CHP:Telratolimod solution prepared in Example 2 was administered via tail vein injection to 5 mice (amount of Telratolimod: 84.5 μg). As a control, 5 mice were prepared for a CHP:Telratolimod-untreated group. The tumors were excised 1 day after the final administration, and CD8-positive T cells and NK cells infiltrating the tumors were detected by flow cytometry. Significance tests were performed using one-way ANOVA.

Results

Figure 9:
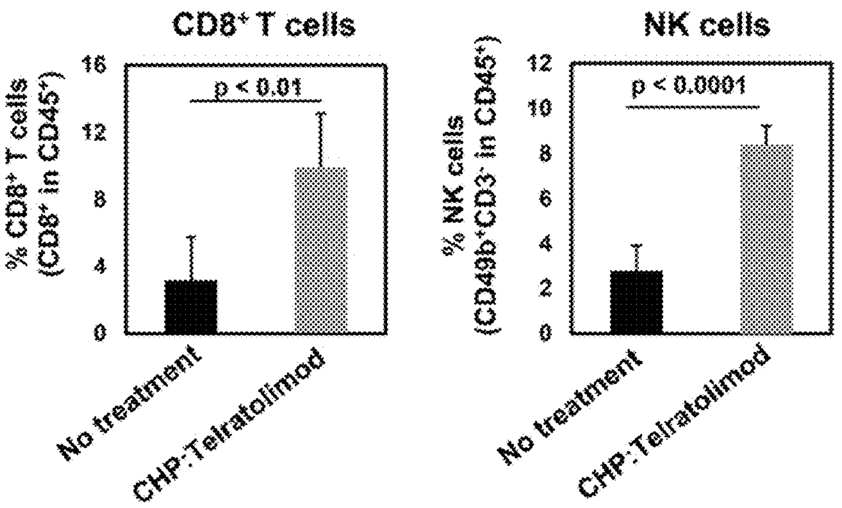
FIG. 9 shows the results of Test Example 15. The vertical axis indicates the ratio of CD8-positive T cells and NK cells infiltrating into the tumor, and the horizontal axis indicates the test drugs added.

The results are shown in FIG. 9. The administration of CHP:Telratolimod significantly increased the number of CD8-positive T cells and NK cells infiltrating into the tumors. These results indicate that CHP:Telratolimod has the effect of increasing the infiltration of CD8-positive T cells and NK cells, which are major effector cells involved in anti-tumor responses, into tumors, suggesting that this is one of the mechanisms of the high antitumor effect of CHP:Telratolimod in Test Example 6.

Test Example 16. Analysis of Cancer Antigen-Specific CD8-Positive T Cells in Mouse Allogeneic Tumor Transplantation Model An MC38 mouse allogeneic tumor transplantation model was prepared in the same manner as in Test Example 6. On days 7, 9, and 12 after cell transplantation, the CHP:Telratolimod solution prepared in Example 2 was administered via tail vein injection to 5 mice (amount of Telratolimod: 84.5 μg). As a control, 5 mice were prepared for a CHP:Telratolimod-untreated group. One day after the final administration, the spleens were excised, and splenocytes were prepared. The cells were stimulated with a peptide from MuLV p15E, which is a cancer antigen expressed in MC38 cells, or, as a negative control, a peptide from TRP2, which is a cancer antigen expressed in melanoma cells, and the cells were permeabilized. Then, CD8-positive T cells were analyzed by flow cytometry using an anti-IFN-γ antibody. Significance tests were performed using unpaired t-tests.

Results

Figure 10:
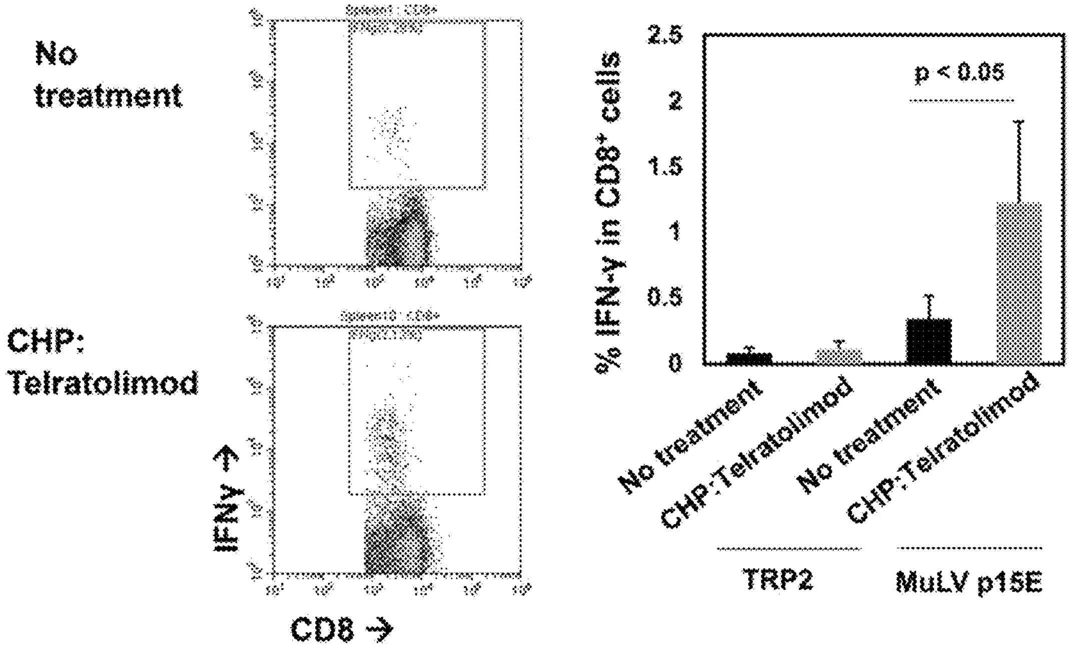
FIG. 10 shows the results of Test Example 16.

The results are shown in FIG. 10. In the mice administered CHP:Telratolimod, the number of CD8-positive T cells that became IFN-γ-positive upon stimulation with the peptide from MuLV p15, which is a cancer antigen of MC38 cells, was significantly increased compared to the CHP:Telratolimod-untreated group. On the other hand, stimulation with TRP2 peptide as the negative control showed no change in the number of CD8-positive T cells that became IFN-γ positive compared to the untreated group. These results indicate that CHP:Telratolimod has the effect of increasing CD8-positive T cells specifically reactive to MC38 cancer cells, suggesting that this is one of the mechanisms of the high antitumor effect of CHP:Telratolimod in Test Example 6.

Test Example 17. Antitumor Evaluation in Mouse Allogeneic Tumor Transplantation Model (4)

A mouse allogeneic tumor transplantation model was prepared by intradermally administering $5\times10^5$ cells of the mouse melanoma cell line B16F10 into the dorsal skin of mice (C57BL/6NCrSlc, female). On days 7, 9, 11, 14, and 16 after cell transplantation, the CHP:Telratolimod solution prepared in Example 2 was administered via tail vein injection, and an anti-PD-1 antibody (RMP1-14, Bio X Cell) solution and an anti-PD-L1 antibody (10F.9G2, Bio X Cell) solution were each administered intraperitoneally to 10 mice per group (amount of Telratolimod: 160 μg, amounts of anti-PD-1 antibody and anti-PD-L1 antibody: 200 μg). A CHP:Telratolimod and anti-PD-1 antibody combination group and a CHP:Telratolimod and anti-PD-L1 antibody combination group were also evaluated. Tumor sizes were measured on days 7, 9, 11, 14, 16, and 18. The tumor volume was calculated by (long axis×short axis×short axis)/2. The negative control is an untreated group.

Results

Figure 11:
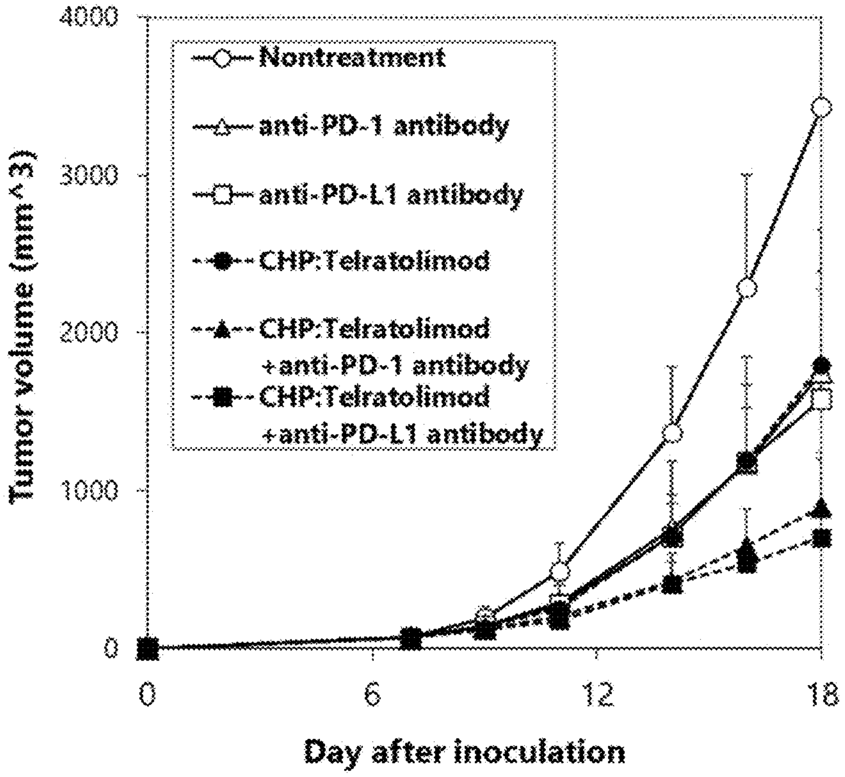
FIG. 11 shows the results of Test Example 17. The vertical axis indicates the tumor volume, and the horizontal axis indicates the number of days since the day cancer cells were implanted intradermally, which was regarded as day 0. The legend indicates test drugs.

The results are shown in FIG. 11. The CHP:Telratolimod-treated group, the anti-PD-1 antibody-treated group, and the anti-PD-L1-treated group showed an antitumor effect of about 50%. On the other hand, the group administered the anti-PD-1 antibody or anti-PD-L1 antibody in combination with CHP:Telratolimod showed an antitumor effect of about 75 to 80%. These results indicate that the combination with CHP:Telratolimod may be expected to have a strong antitumor effect in cancers in which the antitumor effects of the anti-PD-1 antibody and anti-PD-L1 antibody are limited (so-called cold tumors).

The invention claimed is:

1. A solution comprising a complex comprising a modified polysaccharide containing a hydrophobic group, and Telratolimod, wherein the polysaccharide that forms the modified polysaccharide comprises pullulan, and the hydrophobic group comprises a hydrophobic group having a sterol skeleton.

2. The solution according to claim 1, wherein the modified polysaccharide has a weight average molecular weight of 5000 to 2,000,000.

3. The solution according to claim 1, wherein the complex is gel particles.

4. The solution according to claim 3, wherein Telratolimod is contained within the gel particles.

5. The solution according to claim 1, wherein the mass ratio of the modified polysaccharide to Telratolimod (mass of modified polysaccharide/mass of Telratolimod) is 2 to 20.

6. The solution according to claim 1, wherein the complex has a scattering intensity average particle size of 10 to 200 nm.

7. The solution according to claim 1, which is used in combination with an immune checkpoint inhibitor.

* * * * *